United States Patent [19]

Mikuriya et al.

[11] Patent Number: 4,832,487
[45] Date of Patent: May 23, 1989

[54] TEST SYSTEM FOR OPTICAL DISKS

[75] Inventors: Kenta Mikuriya; Masuo Hanawaka; Akira Ohya; Hideo Hirukawa; Shoji Uehara; Kenichi Yamakawa, all of Tokyo, Japan

[73] Assignee: Yokogawa Electric Corporation, Tokyo, Japan

[21] Appl. No.: 100,190

[22] Filed: Sep. 23, 1987

[30] Foreign Application Priority Data

Dec. 18, 1986 [JP] Japan .................................. 61-302186

[51] Int. Cl.$^4$ ............................................ G01N 21/88
[52] U.S. Cl. .................................... 356/243; 356/237; 369/53
[58] Field of Search ....................... 356/237, 239, 243; 369/45, 46, 33; 250/252.1, 201

[56] References Cited

U.S. PATENT DOCUMENTS 4,508,450 4/1985 Ohshima et al. ..................... 356/237

Primary Examiner—Vincent P. McGraw
Assistant Examiner—S. A. Turner
Attorney, Agent, or Firm—Moonray Kojima

[57] ABSTRACT

A test system for optical disks, comprising a spindle motor for bearing and rotating an optical disk at a constant speed; a measuring head, comprising focus servor and tracking servo mechanisms for causing the focal point of a laser beam irradiating the optical disk to follow the guide groove of the disk, for generating an output signal proportional to the intensity of the reflected beam coming from the optical disk; a feed mechanism for moving the measuring head in a radial direction of the optical disk; a control circuit for controlling the operations of the spindle motor, the focus servo and tracking servo mechanism of the measuring head, and the feed mechanism; a measurer for performing desired measurements in response to the output signal from the measuring head; and a computer for commanding the control circuit and the measurer and for processing the measured data of the measurer, whereby all the measurements are accomplished with the guide groove of the disk being under the focus and tracking servos.

7 Claims, 10 Drawing Sheets

TEST SYSTEM FOR OPTICAL DISKS

BACKGROUND OF THE INVENTION

1. Field of Invention.

This invention relates to an optical disk test system for measuring the recording characteristics of optical disks.

2. Description of the Prior Art.

Generally, the recording characteristics of optical disks depend upon whether the recorded information can be correctly reproduced, and are based upon the error rate. This error rate is not sufficient for grasping the content or tendency of the errors which have occurred in the optical disks. These measurement results cannot be exploited for quality controls in the manufacturing process of the optical disks. Thus, in the optical disk test system, the recording characteristics of the optical disks have to be divided into several items for measurements. More specifically, the magnitudes of signals can be grasped by measuring the reflectivity. The optimum quantity of light for writing and reading and the qualities signals can be caught with the carrier/-noise ratio (referred to as CNR) and their details can be grasped through crosstalk and waveform analysis.

On the other hand, the transparency is utilized for evaluating the optical absorption and lifetime of a recording film. However, if the CNR is more than 45 dB, the main cause of errors is flaws (i.e. defects). The length or size of defects and their distribution are useful measures for evaluating the burst errors and for improving the production process. Hence, the measurements of defects are effective for evaluating the recording characteristic of the optical disks, and the measurements of reflectivity relating thereto are the center of the test system. The presence or absence of defects are detected in terms of changes in the quantity of reflected light on the recording film surface.

FIG. 1 is a diagram depicting a conventional reflectivity measuring system comprising an optical disk 1, a recording film 11 of the disk 1, a laser beam source 31, a half mirror HMR1, and a light receiving element 37. Optical disk 1 is irradiated with a parallel beam having a diameter of about 1 mm. The reflected beam is received by light receiving element 37 so that the reflectivity of disk 1 is determined in terms of the intensity of the reflected beam.

In the reflectivity measuring system based on this principle, however, the reflected beams from film 11 and the surface of disk 1 interfere so that only the former reflected beam cannot be accurately measured. Since the parallel beam is used for measurements, on the other hand, the measured values will change greatly even in case the angle of incidence on optical disk 1 changes only slightly. Because the beam has a large diameter, moreover, minute defects cannot be finely detected. Since the parallel beam has a state different from that for practical reproduction, it is impossible to determine reflectivity conforming to practical reproduction. In addition, the system under consideration has an optical system which is different in construction from those used for measuring the CNR and cross talk so that a plurality of measuring systems are required for evaluating a series of different recording characteristics.

SUMMARY OF THE INVENTION

Accordingly, an object of the invention is to provide a simple optical disk test system which can overcome the deficiencies and disadvantages of the prior art.

Another object is to provide a test system which can determine a reflectivity conforming to practical reproduction and which can use an optical system which is shared with measurements of the CNR and crosstalk, so that the system itself can measure a series of different recording characteristics without requiring an additional system.

The foregoing and other objects are attained by the invention which encompasses a test system for optical disks comprising a spindle motor for bearing and rotating an optical disk at a constant speed; a measuring head, including focus servo and tracking servo mechanism for causing the focal point of a laser beam irradiating the optical disk to follow the guide groove of the optical disk, for generating an output signal proportional to the intensity of the reflected beam coming from the optical disk; a feed mechanism for moving the measuring head in a radial direction of the optical disk; a control circuit for controlling the operations of the spindle motor, focus servo and tracking servo mechanisms of the measuring head, and the feed mechanism; a measurer for performing desired measurements in response to the output signal from the measuring head; and a computer for commanding the control circuit and the measurer and for processing the measured data from the measurer.

DETAILED DESCRIPTION OF THE PREFERRED EMBODIMENTS

Figure 1:
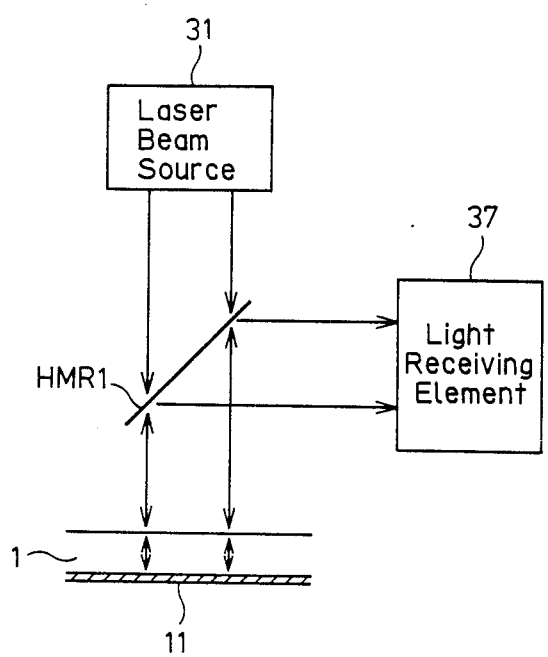
FIG. 1 is a diagram depicting a conventional reflectivity measuring system.
Figure 2:
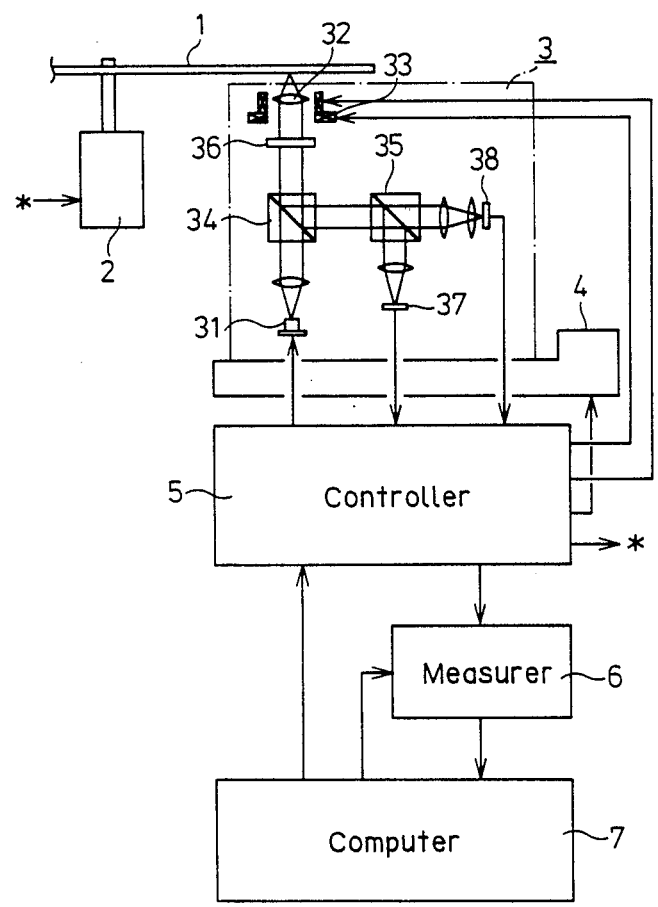
FIG. 2 is a diagram depicting an illustrative embodiment of the invention.

In FIG. 2, the components which are similar to those of FIG. 1 have the same reference numerals. In addition, the embodiment comprises a spindle motor 2 for bearing and rotating an optical disk 1 at a constant speed; and a measuring head 3 which is equipped with focus servo and tracking servo mechanisms for causing the focal point of a laser beam irradiating optical disk 1 to follow the guide groove of disk 1. Measuring head 3 generates an output signal proportional to the intensity of the reflected beam coming from disk 1 and comprises a laser beam source 31; a focusing lens 32; a lens actuator 33; beam splitters 34 and 35; quarter wave ($\lambda/4$) plate 36 and light receiving elements 37 and 38. Thus, measuring head 3 is an optical system for generating an output signal proportional to the intensity of the reflected beam coming from disk 1 through light receiving element 37; and an optical system for detecting the focal state on disk 1 through light receiving element 38 so as to obtain feedback signals for the focus servo and tracking servo mechanisms. Also provided are feed mechanisms 4 for moving measuring head 3 in the radial direction of optical disk 1; a controller 5 for driving lens actuator 33 in accordance with the output of light receiving element 38 to operate the focus servo mechanism and the tracking servo mechanism and to control the operations of spindle motor 2 and feed mechanism 4; a measurer 6 for performing desired measurements, such as the measurement of reflectivity in response to the output signal generated by measuring head 3; and a computer 7 for commanding controller 5 and measurer 6 and for processing the measurement data obtained from measurer 6.

Figure 3:
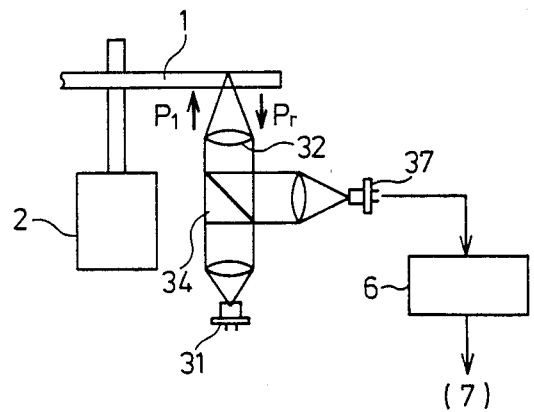
FIG. 3 is a diagram depicting the principle of measuring reflectivity.

The operation sequences of the individual components are selected for the desired measurements in response to the commands of computer 7. The principles and operations of the individual measurement items will now be described with reference to FIG. 3 which depicts the principles of reflectivity measurement. The measurement of reflectivity is effective for grasping not only the reflectivity of the recording film itself but also the unevenness of the reflectivity of the entire surface of the disk.

The beam emanating from focusing lens 32 is a converging one, which is focused like the other measurements on the recording face of disk 1 so that the reflectivity is measured for disk 1 being rotated. At this time, if the power of the light emanating from lens 32 is designated as Pl whereas the optical power of the light reflected from optical disk 1 is designated Pr, the reflectivity Ref is determined by the following equation $$Ref = Pr/Pl \, (\%)$$

If the reflectivity is measured with the recording face of disk 1 being focused, a more accurate reflectivity measurement, in conformity with the practical reproduction state, can be performed to ensure high resolution because there occurs no interference between the reflected lights coming from the recording face and the optical disk surface.

Defects are detected by making use of changes in the amount of reflected light (i.e. the reflectivity). This amount of reflected light will increase or decrease in dependence upon the kinds of defects. For defect detection, the surface of disk 1 is scanned to generate an output signal proportional to the reflectivity from measuring head 3. This output signal is compared in measurer 6 with a constant threshold level to generate a pulse signal (i.e. defective pulses) according to the reduction of reflectivity (due to occurrence of defects). Here, by making the threshold level variable, the size of defects to be detected can be optimized, and the kind of target defects can be restricted. Since the width of the defective pulses is proportional to the size or length of the defects, not only the existence, but also, the length of the defects can be detected by making a count with a reference clock, for example of 16 MHz.

The entire surface of disk 1 usually has numerous defects that cannot be detected in real time. Thus, the test system of the invention, adopts a subdivision method, wherein defective pulses are counted for one pulse and instantly subdivided into one of seven predetermined grades so that the integrated value of the grades is counted up. In order to make a defect map, one track is divided into 1,024 parts, which is further subdivided with a width of 1 mm in the radial direction into one block. In each block, an integration is made for each grade. If the data of all the blocks in a designated area are thus detected, computer 7 makes a bar graph of the total numbers of defects of the seven grades and computes and displays the defect distribution of the entire surface of the optical disk.

Figure 4:
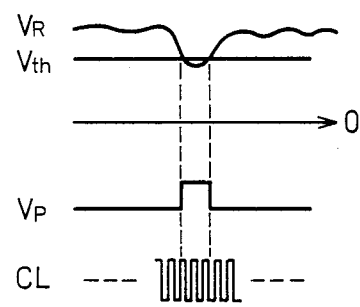
FIGS. 4 and 6 are waveform charts depicting principle of measuring defects.

FIG. 4 is a waveform chart which illustrates the principle of defect measurements, wherein $V_R$ denotes an output signal proportional to the reflectivity; Vth is the threshold level; $V_P$ is a defective pulse; and CL are reference lock pulses. Depicted is the case wherein the reflectivity drops in accordance with occurrence of defects.

Figure 5:
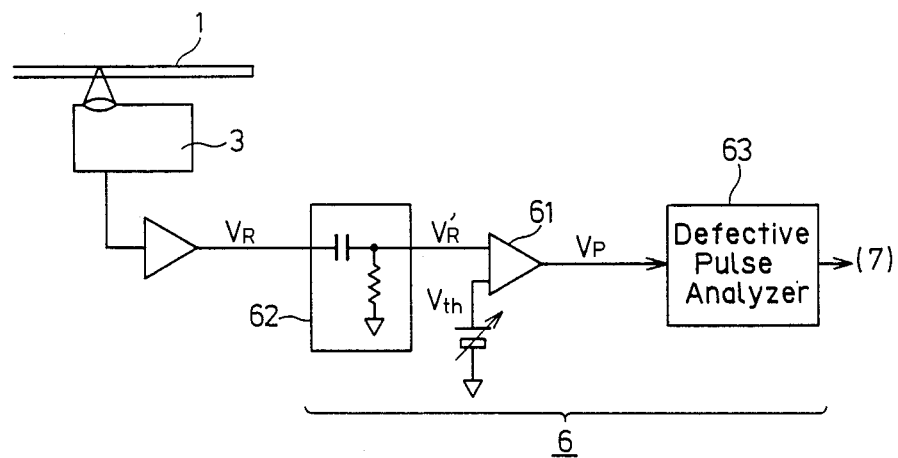
FIG. 5 is a diagram depicting a measurer for defect measurements.

FIG. 5 depicts a measurer 6 comprising a comparator 61 for comparing output signal $V_R$ with constant threshold level Vth; a high pass filter 62 disposed upstream of comparator 61; and a defective pulse analyzer 63 made responsive to the defective pulses $V_P$ issued from comparator 61 to perform the above specified analysis such as the grading according to the size of defects.

Figure 6:
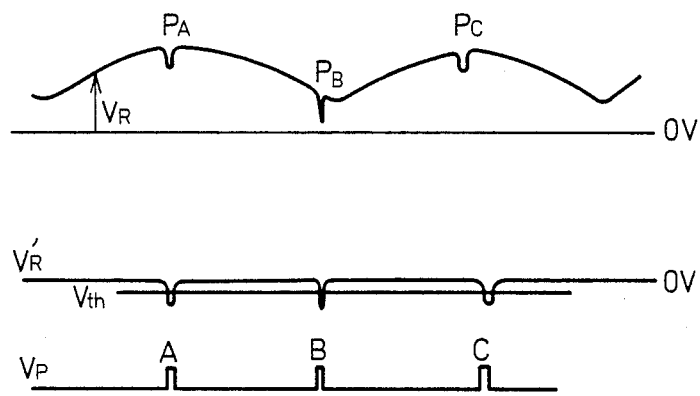

In measurer 6, an output signal $V_R'$ applied to comparator 61 has only a high frequency component so that the defects can be reliably detected, even in case the output signal $V_R$ is highly fluctuated, as shown in FIG. 6, due to the unevenness of the reflectivity on the disk surface. Here, in output signal $V_R$, the level fluctuations due to the unevenness of the vapor deposition of the recording film of disk 1 are about several tens to several hundreds Hz, and the level fluctuations due to the presence of defects are about 10 KHz or more. Thus, if the cut-off frequency of high pass filter 62 is selected at about 1 KHz, only the level fluctuations of output signal $V_R$ due to the presence of the defects can be detected without fail.

Figure 7:
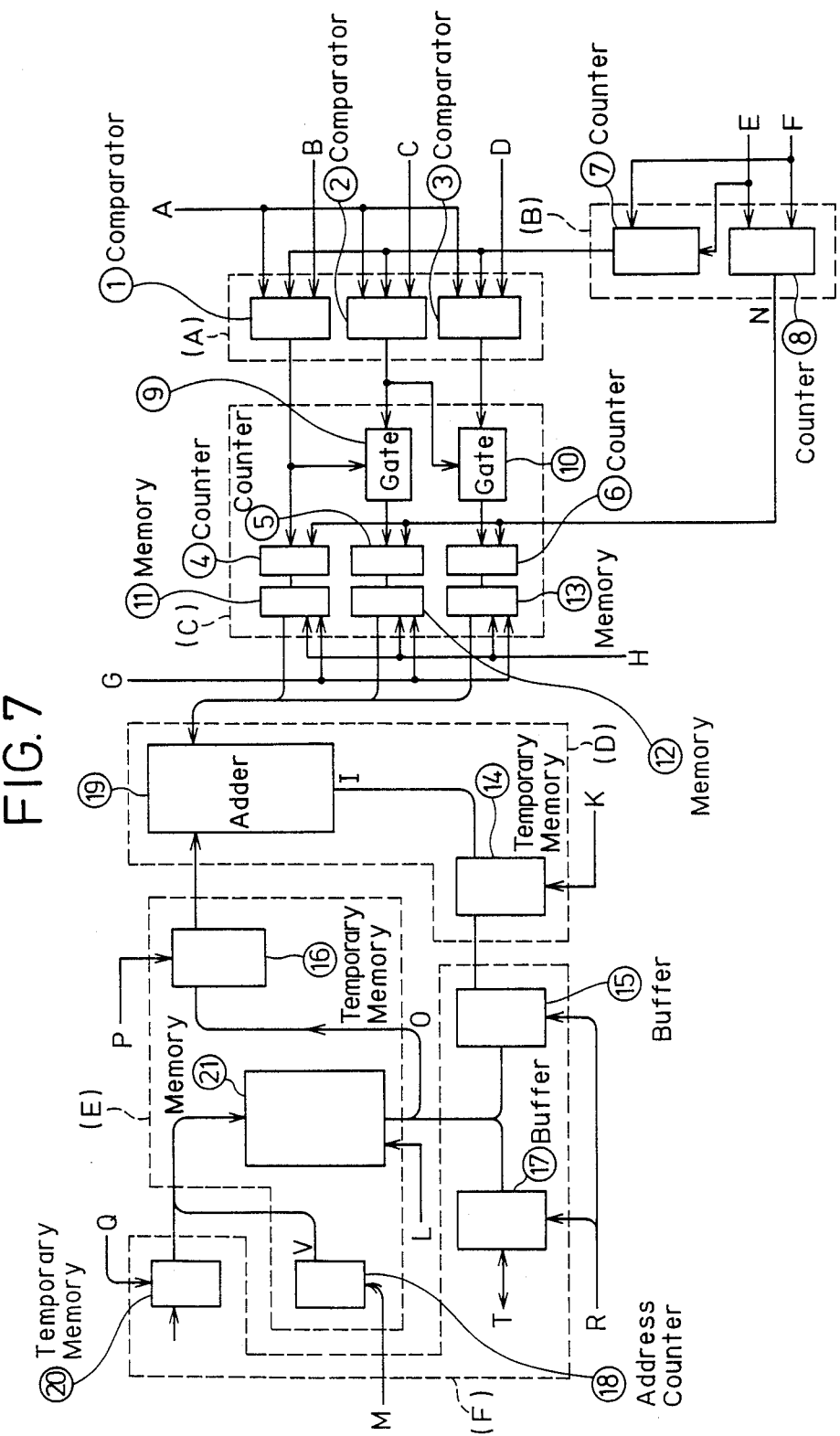
FIG. 7 is a block diagram depicting a specific defective pulse analyzer.

FIG. 7 depicts a defective pulse analyzer 63 wherein the number of defects is subdivided into three grades and counted. In FIG. 7, unit (A) enclosed by broken lines is a defect length setting unit which has comparators ①, ② and ③; unit (B) enclosed by broken lines is a defect length judging unit which comprises a counter ⑦ for counting the reference clock pulses CL in accordance with defective pulses $V_P$ to detect the size or length of the defects, and a counter ⑧ for comparing the defective pulses $V_P$ and the reference clock pulses CL to detect the end of the defects and to generate a signal N; unit (C) enclosed by broken lines is an interval data counting unit which comprises counters ④ to ⑥ and memories ⑪ to ⑬ corresponding to the comparators ① to ③, and gates ⑨ and ⑩ to be opened sequentially in accordance with the output states of comparators ① to ③ and which is operative to count the number of defective pulses $V_P$ for each grade; unit (D) enclosed by broken lines comprises temporary memory ⑭ and adder ⑲; unit (E) enclosed by broken lines is a total data memory unit which has a memory area corresponding to the blocks set on the optical disk surface; and unit (F) enclosed by broken lines is a data input/output control unit for controlling the reading and writing of data from and in total data memory unit (E).

The defect length setting unit (A) comparators ① to ③ have applied thereto a clock signal A for setting the reference value of the length of the defects and set at arbitrary threshold values by latch signals B to D. In this case, the threshold values of comparators ① to ③ are made different. For example, the threshold value of comparator ① is the shortest; the threshold value of comparator ② is longer than that of comparator ①; and the reference value of comparator ③ is set longer than that of comparator ②.

Now, the output of counter ⑦ a value according to the size of the defect is sent to comparators ① to ③ so that it is compared with their respective threshold values. If, at this time, the defect length or size is within the range of the threshold value set in comparator ①, comparator ① generated an output enabling counter ④. At the instant when signal N informing the end of the defect range is generated by counter ⑧, counter ④ counts the signal N and sets the counted value of +1. At this time, gates ⑨ and ⑩ are closed so that counters 5 and 6 do not count.

If, on the other hand, the defect length or size exceeds the range of the threshold value set in comparator ①, the output of comparator ① is inverted to prohibit the counting of counter ④ and opens gate ⑨. As a result, signal N from counter ⑧ is counted in counter ⑤ so that the counted value takes +1.

On the other hand, if the defect length or size exceeds the range of the threshold value set in comparator ②, only counter ⑥ is enabled to count signal N coming from counter ⑧ like the foregoing operation. In these ways, counters ④ to ⑥ count the number of defects for the respective grades.

Now, measuring head 3 is scanning the optical disk surface along the guide groove so that defective pulses $V_P$ applied to defect size or length judging unit (B) are the sequentially inputted data belonging to the plural blocks on disk 1. In the analyzer 63, the memory areas of different blocks are thus assigned to a memory ㉑ of total data memory unit (E) so that the respective counted values of counters ④ to ⑥ obtained from defective pulses $V_P$ are added sequentially of the data of the corresponding memory areas. Thus, if the counted value of memory ㉑ is read out by designating its memory area, the data of each block on the disk surface can be arbitrarily reproduced.

At the instant when measuring head 3 passes the boundary of a block, for example, an end signal H is generated so that memories ⑪ to ⑬ store the counted values of counters ④ to ⑥ for that period of time. These stored values of memories to ⑪ to ⑬ are read in an adder ⑲ of data adding unit (D) in response to a signal G before a next end signal H is generated. In memory ㉑, moreover, the data (which take a level 0 in the initial state) of the memory area corresponding to that block are sent through a temporary memory ⑯ to adder ⑲ in response to a control signal P so that they are added to the data of memories ⑪ to ⑬. The data I thus added are stored in a temporary memory ⑭ in response to a timing signal K. The data I thus stored pass through a buffer ⑮ and are stored in the initial memory area of the memory ㉑ in response to a timing signal L. At this time, an address count ⑱ operates in response to a control signal M so that a memory address signal V changes to switch the memory areas to rewrite the data.

By repeating these sequences, the defective pulses $V_P$ applied can be divided into blocks and can be subdivided into respective grades and stored in memory ㉑. In order to read out the data from memory ㉑, an arbitrary address is designated from a temporary memory ⑳ in response to a control signal Q in place of the address signal V coming from address counter ⑱, and buffer ⑮ is turned OFF whereas a buffer ⑰ is turned on by a control signal R. In the sequences described above, a defective data signal O of an arbitrary block from memory ㉑ can be read out and outputted as a signal T to buffer ⑰. This signal T is inputted to computer 7 and processed to and displayed as a bar graph or a defect map for each grade.

Figure 8:
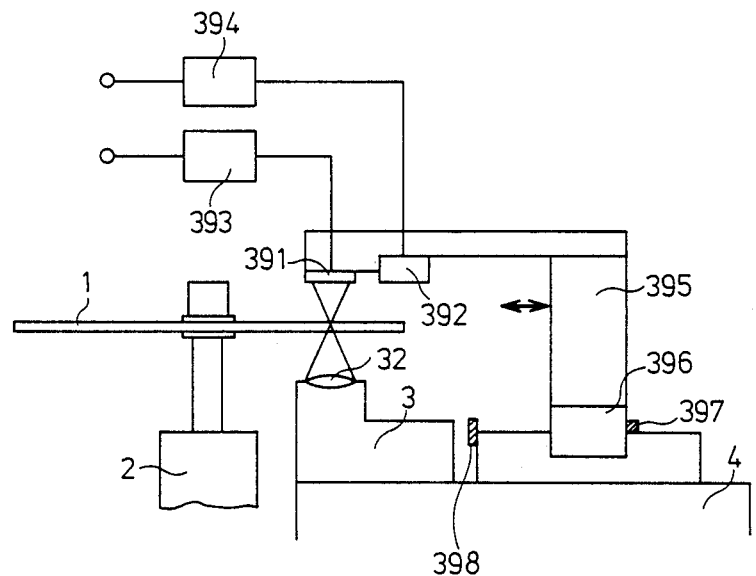
FIG. 8 is a diagram depicting measurement of transparency.

FIG. 8 depicts a transparency measurement system comprising photodiode 391 for measuring the optical power of a laser beam incident through an optical disk 1; a calibrating photodiode 392 which has been calibrated in advance by a reference optical power measurer for calibrating the intensity of the beam emanating from focusing lens 32; current voltage converters 393 and 394 for converting the output currents of photodiode 391 and calibrating photodiode 392, respectively into voltage signals; and a holder 395 for holding photodiode 391 and calibrating photodiode 391 integrally. Holder 395 is carried on feed mechanism 4 for arranging the light receiving elements selectively in a light receiving position to face measuring head 3 through optical disk 1. The system further comprises slide mechanism 396 for sliding holder 395 in the rightward and leftward directions of the unnumbered arrows, as depicted; and stoppers 397 and 398 for regulating the slide position of holder 395. Slide mechanism 396 and stoppers 397 and 398 are provided to facilitate calibration of the optical power of the emanating beam in measuring head 3. By sliding holder 395, photodiode 391 or calibrating photodiode 392 can be selectively moved to the light receiving position.

FIG. 8 shows the state of measurement of the transparency, wherein holder 395 is fixed at the side of stopper 397 so that photodiode 391 is positioned in the light receiving position. In the transparency measurement system, the ratio, of optical power of the laser beam emanating from focusing lens 32 to the optical power of the laser beam incident upon photodiode 391, is measured as the transparency of the disk 1. Moreover, focusing lens 32 is subjected to the focus servo and tracking servo so that the point of measurement is arbitrarily selected by the rotation of spindle motor 2 and the feed of feed mechanism 4.

Figure 9:
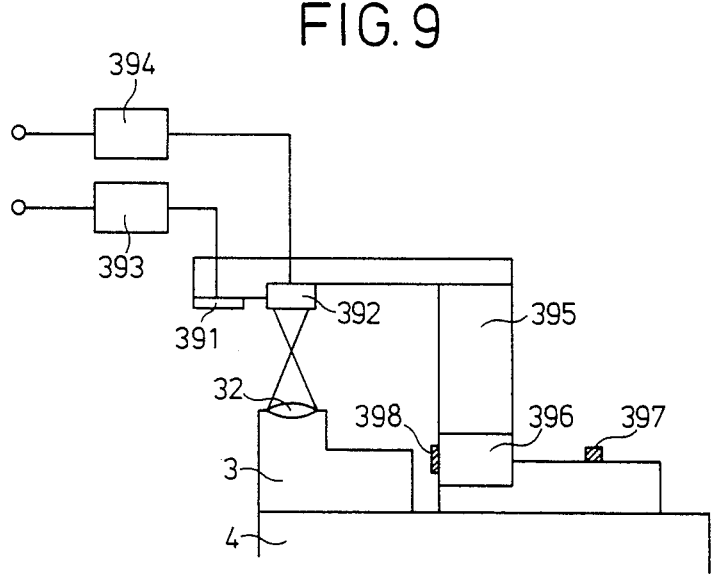
FIG. 9 is similar to FIG. 8 but depicts measurement of optical power calibrations.

In this system of FIG. 8, the optical power of the laser beam emanating from focusing lens 32 has to be calibrated in advance. FIG. 9 depicts means for calibrating the optical power, wherein holder 395 is fixed at the side of stopper 398, and calibrating photodiode 392, in place of photodiode 391, is positioned in the light receiving position. At this time, optical disk 1 is dismounted from spindle motor 2.

Thus, measuring photodiode 391 and calibrating photodiode 392 are integrally held on common holder 395, and slide mechanism 396 is added to holder 395. Then, measuring and calibrating photodiodes 391 and 392 can be selectively moved to the light receiving position so that the optical power can be easily calibrated without any exchange of photodiodes.

Figure 10:
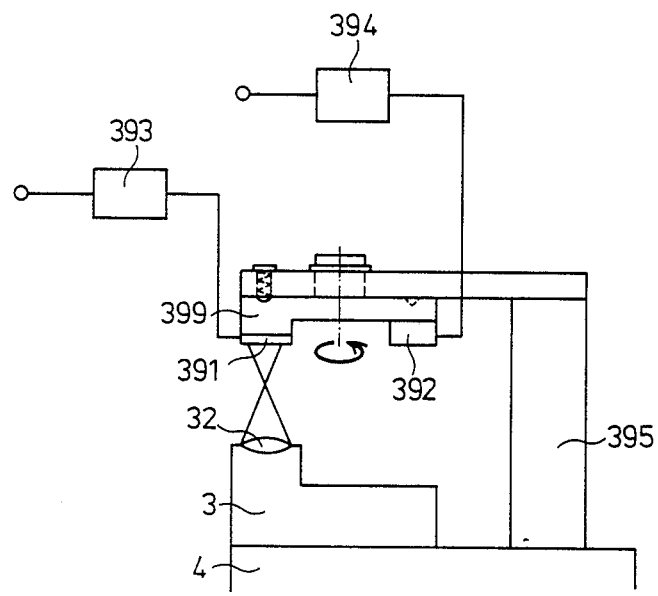
FIGS. 10 and 11 are diagrams depicting another holder.

FIG. 10 depicts another holder 395 in a system comprising a rotary disk 399 which is positioned by a detente mechanism, as one example of the slide mechanism for changing the relative positions of the two photodiodes. Rotary disk 399 is rotatably mounted on holder 395. Photodiode 391 and calibrating photodiode 392 are carried in symmetrical positions on rotary disk 399, and holder 395 is so fixed on feed mechanism 4 that the photodiode 391 or the photodiode 392 is positioned at predetermined light receiving position.

Figure 11:
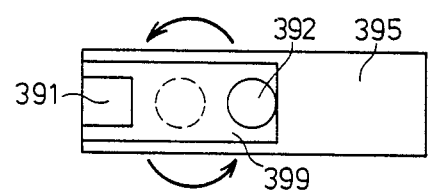

FIG. 11 depicts rotary disk 399 from a bottom view. When rotary disk 399 is rotated, measuring photodiode 391 and calibrating photodiode 392 are selectively brought into the predetermined light receiving position.

Figure 12:
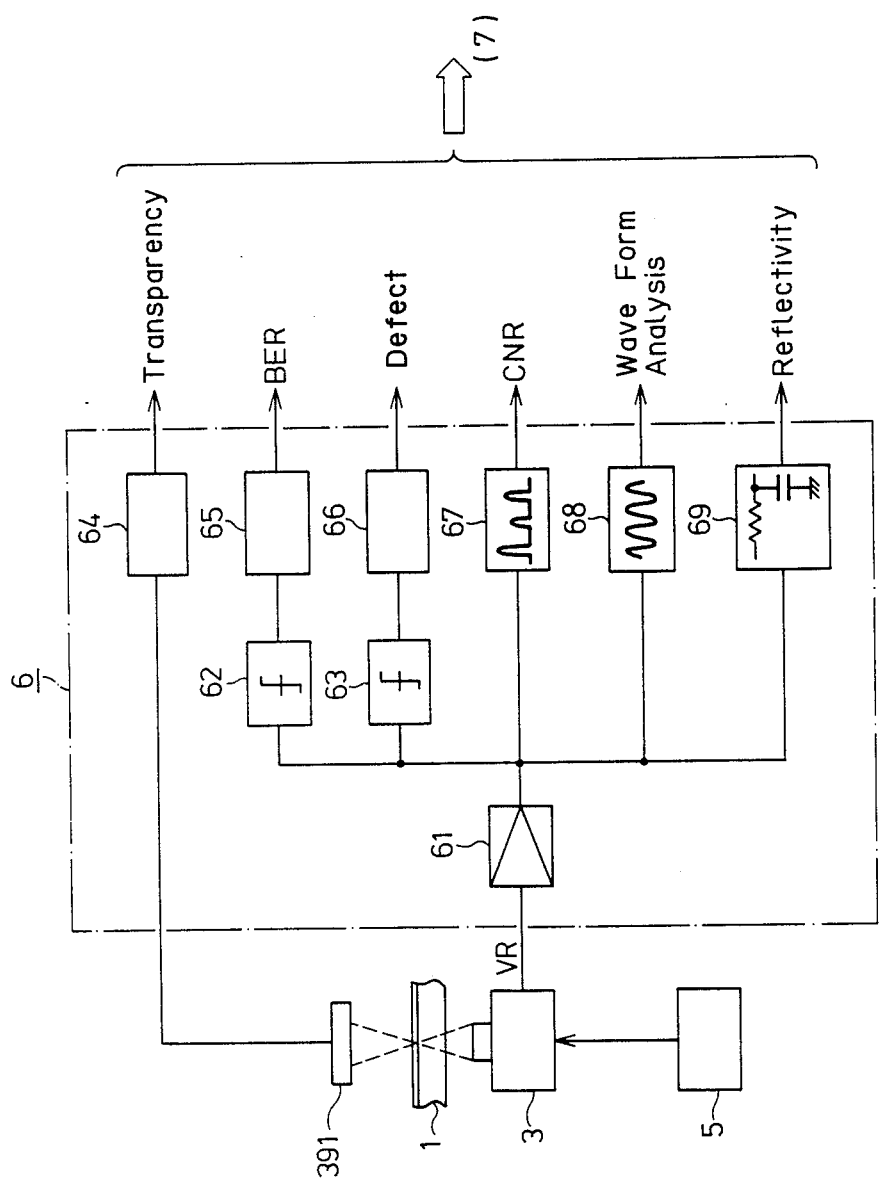
FIG. 12 is a block diagram depicting another measurer.

The measuring technique heretofore described is intrinsic to the invention. The measuring system of the invention, which can also measure conventional items, is shown in block form in FIG. 12, wherein are provided an amplifier 61 for amplifying the output signal $V_R$ of measuring head 3 proportional to the reflected beam from optical disk 1; comparators 62 and 63; a transparency measuring circuit 64 for measuring the transparency of the optical disk 1 from the output of photodiode 391; numeral bit error rate (also referred to as BER) measuring circuit 65; a defect measuring circuit 66; a carrier/noise ratio. (or CNR) measuring circuit 67; a waveform analyzing circuit 68 for measuring jitters or the like; and a reflectivity measuring circuit 69. The operations of the measuring circuits are selected by computer 7, as previously described, and the measured data are sent to computer 7 so that they may be appropriately processed.

In the conventional optical disk test system, reflectivity, or defects, and transparency are measured with the recording face of the optical disk being subjected to the focus servo and the tracking servo. The optical system of the invention can be shared to measure the BER (bit error rate) and CNR (carrier/noise ratio), so that a series of different recording characteristics can be measured using the same single system.

Next, the calibrating system in the test system of the invention will be described. Generally, the measuring system is calibrated before the various characteristics of the disk are measured. For this calibration, there are a variety of methods, of which the method of using standard specimens having known values is convenient because the measuring system including the detectors and the electric circuits can be once calibrated as a whole.

Figure 13:
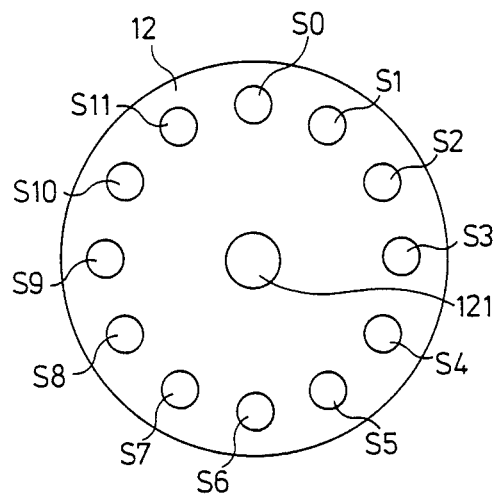
FIG. 13 is a top plan view depicting an illustrative calibrating reference plate used for calibration.
Figure 14:
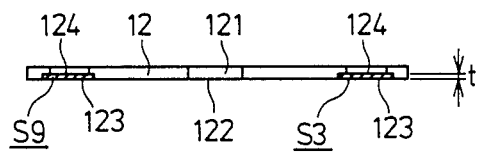
FIG. 14 is a cross-sectional view of FIG. 13.

FIG. 13 and FIG. 14 depict a calibrating reference plate which is used for such calibrations and comprises standard specimens S0 to S11 evaluated at predetermined reference values; a table 12 for holding the standard specimen S0 to S11 on a common circumference; a clamp 121 disposed at the center of table 12; and a clamp face 122 adapted to come at clamp 121 into abutment against a turntable for turning the optical disk. On the other hand, each of standard specimen S0 to S11 is formed with a glass substrate 123 (see FIG. 14) having a thickness t equal to that of the ordinary optical disk, and a reflective or transparent face 124 placed on one surface of glass substrate 123 and made of a dielectric multi-layered film, for example. Table 12 holds standard specimen S0 to S11 such that their reflective or transparent faces 124 are directed upward and so that their height from clamp face 122 is equal to that of the recording face of the ordinary optical disk being clamped. If the disk is of the type in which its substrate is directly clamped, for example, the recording face has a height equal to the thickness so that the standard specimen S0 to S11 are held to have their bottom faces flush with clamp face 122, as shown. If the optical disk has a clamping hub, on the other hand, the height of the standard specimen S0 to S11 is determined by considering the thickness of the hub.

Figure 15:
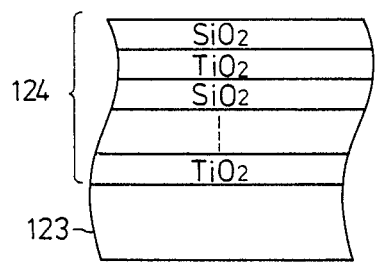
FIG. 15 is a section depicting an example of forming standard specimens S0 to S11 of the calibrating reference plate.

FIG. 15 is a section showing an example of forming the standard specimen S0 to S11. As shown, the reflective transparent film 124 is made of a dielectric multi-layered film so that its reflectivity or transparency is controlled to have predetermined values in accordance with the number of layers. The material for the dielectric multi-layered film used is exemplified by titanium dioxide ($TiO_2$) and silicon dioxide ($SiO_2$). In table 12, no specimen is provided to provide transparency in the positions where the reflectivity is 0% and transparency is 100%.

In the standard plate, an arbitrary one of the standard specimen S0 to S11 can be set above the measuring head without use of any special jig, but, merely by mounting table 12 on the clamp mechanism of the spindle motor through clamp 121. Moreover, standard specimen S0 to S11 are excellent in evenness because each of them has a small area. Since the dielectric multi-layered film making/up the reflective or transparent film 124 is strong against heat, the film will not melt or change its reflectivity even if it is heated to a high temperature as a result of irradiation with laser beams. Glass substrate 123 itself also is stable against high temperature.

Figure 16:
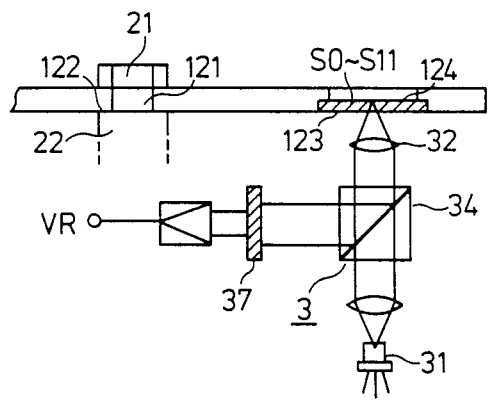
FIG. 16 is a diagram depicting mounting of the calibration reference plate on a spindle motor.

FIG. 16 depicts the reference plate as being mounted on the spindle motor and exemplifies the calibrations in the reflectivity measurements of the optical disk. In FIG. 16, the system comprises an optical disk clamp mechanism 21 of the spindle motor; a turn table 22; a measuring head 3 similar to the foregoing measuring head.

For calibrations, an arbitrary one of the standard specimen S0 to S11 is set above the measuring head 3 merely by turning table 12. Thus, if the interrelationships at this time between the values of standard specimens S0 to S11 and the measured output $V_R$ are plotted and interpolated between the points of measurement, the calibration curve of the entire measuring system, including the optical system such as the focusing lens 32 and the electric circuit sytems, such as photo-detector 37, can be obtained at once. Since the height of the reflective face of each one of the standard specimen S0 to S11 is made equal to that of the recording face of the ordinary optical disk, the gap between measuring head 3 and reflective film 124 becomes equal to that for the measurement of the disk so that the calibrations can be performed under conditions close to those of the actual measurement, such as the condition of the focus servo. Moreover, since the dielectric multi-layered film itself is characterized by small absorption of the laser beam and has a substantially constant sum of the reflected beam and passed beam, it is possible to realize a reference plate which can be used commonly for calibrations of the reflectivity and transparency.

Figure 17:
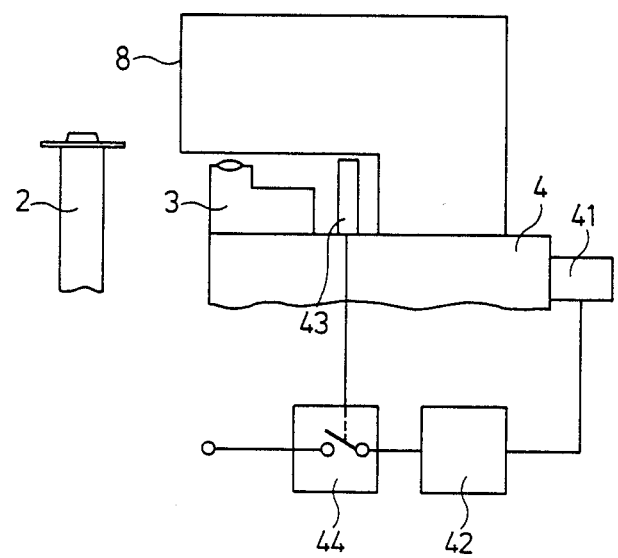
FIG. 17 is a diagram depicting a protecting mechanism for calibrations of a feed mechanism.

A protecting system for the test system of the invention will now be described with reference to FIG. 17 which shows a protecting mechanism for preventing a calibrating member from being injured by errors of the feed mechanism, or the like, when the optical power of the laser beam emanating from measuring head 3 is being calibrated. The system depicted in FIG. 17 comprises a calibrating member 8 which is set on feed mechanism for calibrating measuring head 3. This calibrating member has a photodiode, or the like, for measuring the optical power of the laser beam emitted from measuring head 3. The system further comprises a drive motor 41 of feed mechanism 4; a drive circuit 42 for driving drive motor 41 in response to the command of controller 5, or the like; a detector 43 having a microswitch or a proximity switch for detecting that mcalibrating member 8 is set on the feed mechanism; and a switch 44 inserted into a portion of drive circuit 42 for interrupting drive circuit 42 in response to the detected output of detector 43. Switch 44 can make use of the contact output of detector 43. Moreover, the position of insertion of switch 44 is not limited to the input side of drive circuit 42 and instead may be located at the power line of drive motor 41.

In the protecting mechanism, the switch 44 is always OFF so that drive circuit 42 is interrupted, with calibrating member 8 being set on feed mechanism 4. Even in case the drive command of feed mechanism 4 causes problems or errors in the system, the drive (i.e. power) signal is not applied to drive motor 41 so that the errors of the feed mechanism 4 can be prevented. As a result, calibrating member 8 can be prevented from impinging upon spindle motor 2, or the like, by the errors of the feed mechanism so that it can be protected without fail.

Figure 18:
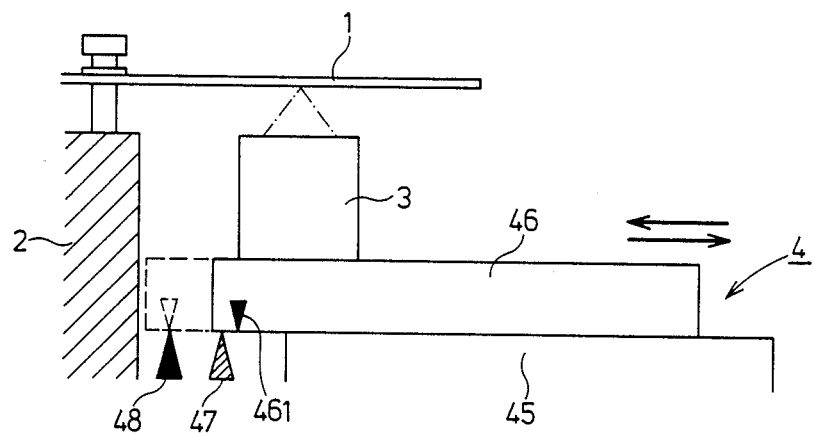
FIG. 18 is a diagram depicting a limiter mechanism for the slide portion of the feed mechanism.

FIG. 18 depicts a limiter mechanism for limiting the moving range of the slide device of feed mechanism 4 so that measuring head 3, or the like, carried on feed mechanism 4 may be prevented from impinging on spindle motor 2 and from being injured. In FIG. 18, there are provided a stationary base portion 45 and a slide portion 46. Measuring head 3, or the like, is carried on slide portion 46 so that the irradiating, or measuring, position of the laser beam is moved in the radial direction of disk 1 as the slide portion 46 slides. Also provided are detectors 47 and 48, made of microswitches or proximity switches, for detecting the passage of the end 461 of slide portion 46.

In the limiter mechanism, the moving velocity of slide portion 46 is decelerated in accordance with the output of detector 4 to halt slide portion 46. This makes it possible to accelerate the moving velocity of slide portion 46 until the limit position is reached and to halt the slide portion reliably with no more than a small amount of overshoot. As a result, measuring head 3, etc, carried on slide portion 46 can be reliably protected against any damage.

Advantageously, all of the measurements are accomplished with the guide groove of the optical disk being under focus and tracking servo. The invention is simple in construction, and can determine the reflectivity in conformity with actual reproduction state. Moreover, the invention comprises an optical system which can be shared to measure the CNR and cross talk. Thus, advantageously, the invention can be used to measure a series of different recording characteristics with use of the same system. Furthermore, advantageously, since the beam of the invention is focused to a small diameter, the resolution of measurements can be increased to accurately detect small defects and their distributions.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A test system for optical disks, comprising
    a spindle motor for bearing and rotating an optical disk at a constant speed;
    a measuring head, comprising focus servo and tracking servo mechanism for causing the focal point of a laser beam irradiating said optical disk to follow the guide groove of said optical disk, for generating an output signal proportional to the intensity of the reflected beam coming from said optical disk;
    a feed mechanism for moving said measuring head in the radial direction of said optical disk;
    a control circuit for controlling the operations of said spindle motor, the focus servo and tracking servo mechanism of said measuring head, and said feed mechanism;
    a measurer for performing desired measurements in response to the output signal of said measuring head; and
    a computer for commanding said control circuit and said measurer and for processing the measured data of said measurer,
    wherein said measuring head comprises a measuring photodiode for measuring the optical power of the laser beam having passed through said optical disk; and a calibrating photodiode for measuring optical power of the laser beam emitted from said measuring head, said measuring and calibrating photodiodes being integrally held by a holder having a slide mechanism.

2. The system of claim 1, wherein said measurer determines the reflectivity of said optical disk from the ration of optical power of said laser beam irradiating said optical disk to optical power of said laser beam reflected by said optical disk.

3. The system of claim 1, wherein said measurer comprises a comparator for comparing the output signal of said measuring head with a constant reference level, to generate a defective pulse of varying width; and a high pass filter disposed upstream of said comparator.

4. The system of claim 3, wherein said measurer further comprises a defect length judging unit for generating a signal proportional to the size of a defect, from the width of said defective pulse; a defect length setting unit for setting the range of a plurality of defect lengths so that the set value is compared with the output signal of said defect length judging unit; and an interval data counting unit for counting the number of generations of said defective pulse respectively for the defect lengths in accordance with the comparison of said defect length setting unit.

5. The system of claim 4, wherein said measurer further comprises a total data memory unit for storing the counted values of said interval data counting unit respectively for blocks set on the surface of said optical disk, said total data memory unit having a memory assigned for the memory areas of the respective blocks so that the counted value of the respective defect lengths by said interval data counting unit may be sequentially added to the data of the memory areas corresponding thereto.

6. A test system for optical disks, comprising:
a spindle motor for bearing and rotating an optical disk at a constant speed;
a measuring head, comprising focus servo and tracking servo mechanism for causing the focal point of a laser beam irradiating said optical disk to follow the guide groove of said optical disk, for generating an output signal proportional to the intensity of the reflected beam coming from said optical disk;
a feed mechanism for moving said measuring head in the radial direction of said optical disk;
a control circuit for controlling the operations of said spindle motor, the focus servo and the tracking servo mechanism of said measuring head, and said feed mechanism;
a measurer for performing desired measurements in response to the output signal of said measuring head; and
a computer for commanding said control circuit and said measurer and for processing the measured data of said measurer,
wherein said measurer comprises a reference plate and calibrates reflectivity and transparency by using said reference plate, said reference plate comprising a plurality of standard specimen, each formed with a reflective or transparent film of a dielectric multi-layered film on one side of a glass substrate having a thickness equal to an ordinary optical disk and evaluated at a predetermined value; a clamp to be commonly clamped by a clamp mechanism of said optical disk, and a substrate for arranging said standard specimen in a common circumference and for holding said standard such that the positions of said reflective or transparent films and the heights of the standard specimen from the clamp face are identical to those of the face of the recording film of the ordinary optical disk to be clamped by said clamp mechanism.

7. A test system for optical disks, comprising
a measuring head for applying a laser beam having predetermined optical power to an optical disk;
a measuring photodiode for measuring the optical power of the laser beam having passed through the optical disk;
a calibrating photodiode for measuring the optical power of the laser beam emitted from the measuring head; and
a sliding holder for integrally holding the measuring and calibrating photodiodes, and capable of selectively moving the measuring photodiode or the calibrating photodiode to a light receiving position.

* * * * *